United States Patent [19]

Kamerling et al.

[11] Patent Number: 5,653,723
[45] Date of Patent: Aug. 5, 1997

[54] METHOD AND APPARATUS FOR PERFORMING KERATOTOMY

[76] Inventors: William Kamerling, 423 Clements Bridge Rd.; Fred D. Allen, Jr., c/o William Kamerling, 423 Clements Bridge Rd., both of Barrington, N.J. 08007

[21] Appl. No.: 356,441

[22] Filed: Dec. 13, 1994

[51] Int. Cl.[6] ................................. A61B 17/00
[52] U.S. Cl. ........................................ 606/166
[58] Field of Search .......................... 606/166, 167

[56] References Cited

U.S. PATENT DOCUMENTS

| | | | |
|---|---|---|---|
| 4,406,285 | 9/1983 | Villasenor et al. | 606/166 |
| 4,619,259 | 10/1986 | Graybill et al. | 606/166 |
| 4,688,570 | 8/1987 | Kramer et al. | 606/166 |

OTHER PUBLICATIONS

RK, AK Templates To Move Surgery From Art to Science by: Bob Kronemyer; Ocular Surgery News; May 15, 1995.
Ocular Surgery News; Sep. 15, 1994, pp. 58, 59.
Review of Ophthalmology; May, 1994, pp. 42–45.

Primary Examiner—Michael Powell Buiz
Assistant Examiner—William Lewis
Attorney, Agent, or Firm—Stuart E. Beck

[57] ABSTRACT

A keratotomy apparatus that comprises a plurality of plates. One of the plates is kept on the eye during the keratotomy. The other plates support corneal thickness sensors and guides that enable both radial and arcuate keratotomy cuts to be made. A keratotomy knife that has cams that cooperate with camming surfaces to guide the keratotomy knife. A keratotomy method comprises the steps of measuring the thickness of the cornea, providing a plurality of keratotomy knife guides, positioning the keratotomy knife guides over the cornea, and making the keratotomy cuts in the cornea.

35 Claims, 5 Drawing Sheets

METHOD AND APPARATUS FOR PERFORMING KERATOTOMY

BACKGROUND OF THE INVENTION

This invention relates to a method for performing a keratotomy and an apparatus for the same.

Keratotomy is the surgical reshaping of the cornea of the eye with a series of radial and/or arcuate cuts that are made in the cornea. The incisions flatten the cornea. This decreases its radius of curvature. Radial cuts correct myopia while arcuate cuts correct astigmatism. It is common to correct both myopia and astigmatism during the same keratotomy procedure.

Figure 1:
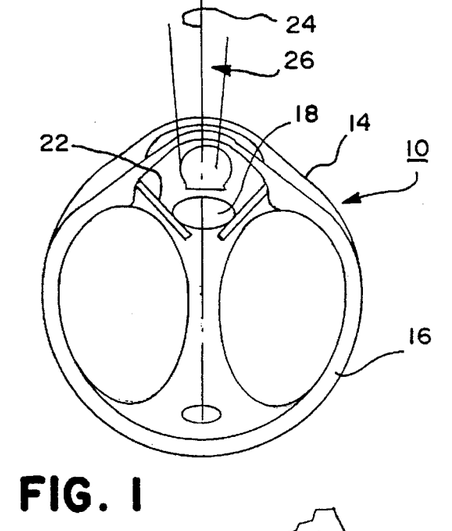
FIG. 1 is a schematic view of a cross-section of an eye.

In FIG. 1 an eye 10 is illustrated schematically. Its outer shape is defined by the cornea 14 and the sclera 16. The cornea 14 is a transparent curved member that is a major site of refraction of light entering the eye. On its perimeter the cornea 14 is connected to the sclera. As is well known, within the eye and behind the cornea are the lens 18 and the iris 22.

The cornea is thinnest at its central area and thicker where it joins the sclera with the thickness ranging from about 0.5 mm in the central area to about 0.8 mm on the periphery. The cornea typically has a diameter of about 11.0 mm to 12.0 mm.

The eye 10 includes a visual axis 24 which passes through the centers of curvature of the inner and outer surfaces of the cornea 14. It also includes a central area having a diameter of about 3.0 mm that is called the optical zone 26.

As presently practiced, the radial cuts are made along lines that pass through the visual axis 24. However, the inner limit of the cut is defined by the optical zone 26. There may be between four and eight radial cuts. The number of cuts and their length are determined by several factors including the age of the patient, the size of the cornea, its thickness and the extent to which the vision is to be corrected. The cuts should not be in the optical zone because they will cause scaring and glare.

The arcuate cuts are made at distance that is about 3.5 mm radially outwardly from the visual axis 26. They are located between the radial cuts, but do not intersect them. Usually there are two arcuate cuts that are diametrically opposed across the visual axis.

The cuts are usually made with a knife having a blade whose depth of cut can be adjusted with micrometer precision. The blades are set so that both the radial cuts and arcuate cuts penetrate about ninety percent of the corneal thickness.

The thickness of the cornea at the outer edge of the optical zone 26 is measured. Usually a pachymeter, which employs ultrasound, is used. Then, the ophthalmic surgeon, using a knife having the thinnest possible blade, sets the depth of the knife blade and makes the radial and/or arcuate cuts as is appropriate. Usually, only one measurement of corneal thickness is made. Nonetheless, it maybe desirable to measure the thickness at several locations since the cornea may have areas of different thickness.

As currently practiced, the keratotomy procedure relies upon marks made on the cornea by the ophthalmic surgeon that indicate where the radial keratotomy cuts are to be made. There may be a risk of inaccuracy and/or harm to the patient. This is because the surgeon is cutting freehand along the marks. Therefore, the actual cuts may deviate from the marks on the cornea. Also, there is risk that the cuts may enter the optical zone and/or they will extend too far toward the sclera, or be too deep and perforate the cornea. The problem is aggravated by the thinness of the blade since its thinness makes it more difficult to control.

Further, when arcuate cuts are made so as to correct astigmatism, there is a risk that the arcuate cuts will intersect the radial cuts since their direction is transverse to the radial cuts thereby distorting vision rather than improving it.

It would be desirable to provide a method and apparatus which simplifies the keratotomy procedure so that the time that it takes can be reduced while its accuracy and safety can be increased.

Thus, with the foregoing in mind the invention relates to an apparatus for performing a keratotomy that comprises a plurality of interchangeable plates. One of the plates is retained on the eye during the keratotomy. The interchangeable other plates support corneal thickness sensors and guides for a keratotomy knife that enable both radial and arcuate cuts to be made in predetermined locations and at predetermined lengths and depths.

In another aspect the invention relates to a plate for use in a keratotomy apparatus that includes inner and outer annular members and a plurality of radially directed keratotomy knife guides that are supported by the annular members.

In still a further aspect of the invention there is provided a keratotomy plate that comprises a plurality of arcuate guides for a keratotomy knife and means for supporting the arcuate guides so that they are located outside of the optical zone when the plate is supported on the eye.

Yet a further aspect of the invention relates to the method of performing a keratotomy which comprises the steps of locating the optical axis of the eye, providing a plurality of keratotomy knife guides, placing the keratotomy knife guides on the cornea with the keratotomy knife guides being spaced from the optical zone of the eye, and making cuts in the cornea at the locations defined by the keratotomy knife guides.

DESCRIPTION OF THE DRAWING

The invention will be better understood and further advantages and uses of it will be readily apparent when considered in view of the following detailed description of exemplary embodiments, taken with the accompanying drawing in which.

DETAILED DESCRIPTION OF THE PREFERRED EMBODIMENTS

Figure 2:
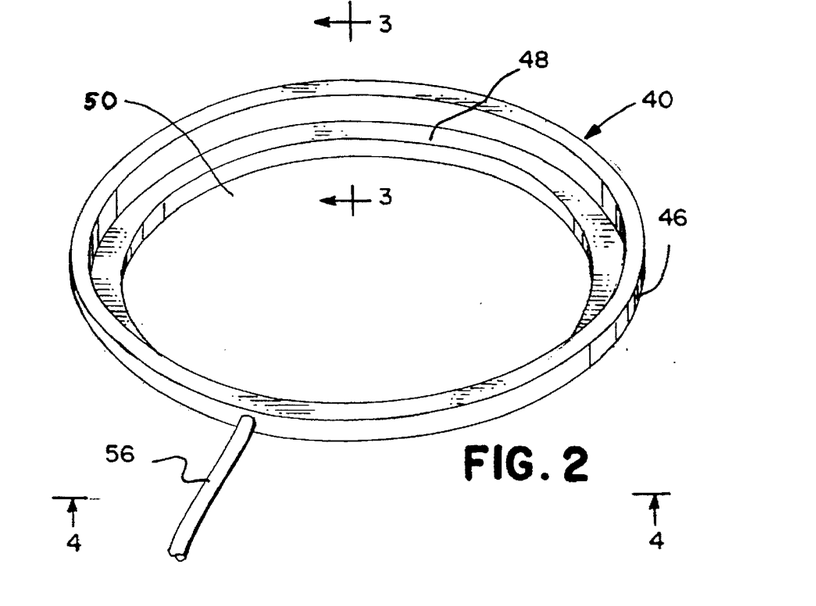
FIG. 2 is a perspective view of one of the plates comprising the apparatus.
Figure 3:
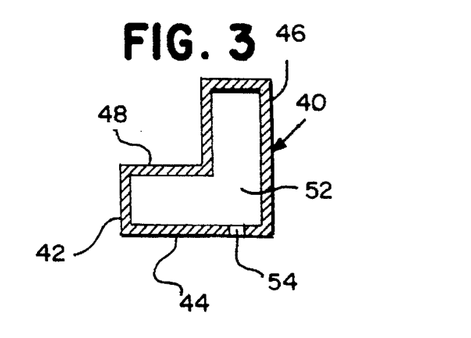
FIG. 3 is a section view taken along line 3—3 of FIG. 2.
Figure 4:
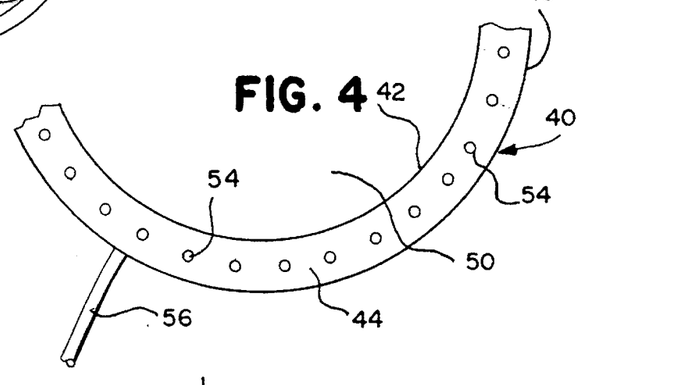
FIG. 4 is a section view taken along line 4—4 of FIG. 2.

Referring to FIGS. 2, 3 and 4 the apparatus includes a first plate comprising an annular ring 40 that is generally "L" shaped in cross-section and having an outer diameter of about 11.0 mm to 12.0 mm so that it can be placed on the cornea 14. It has a horizontally extending base 42 having a bottom surface 44, and an upwardly directed leg 46. The juncture of the base 42 and leg 46 forms an inwardly facing circumferential ledge 48 that in turn defines a large central opening 50.

The annular ring 40 has a hollow interior 52 with a plurality of circumferentially spaced openings 54 in the bottom surface 44 communicating with the hollow interior 52.

An elongated flexible conduit 56 is connected at one end to an opening (not shown) in leg 46. Its other end is connected to a suitable source of vacuum.

The plate 40 is adapted to be placed on the cornea 14. Air is withdrawn from the hollow interior 52 through conduit 56 to retain the plate 40 on the cornea by virtue of the interaction of the openings 54 and the corneal surface.

Figure 5:
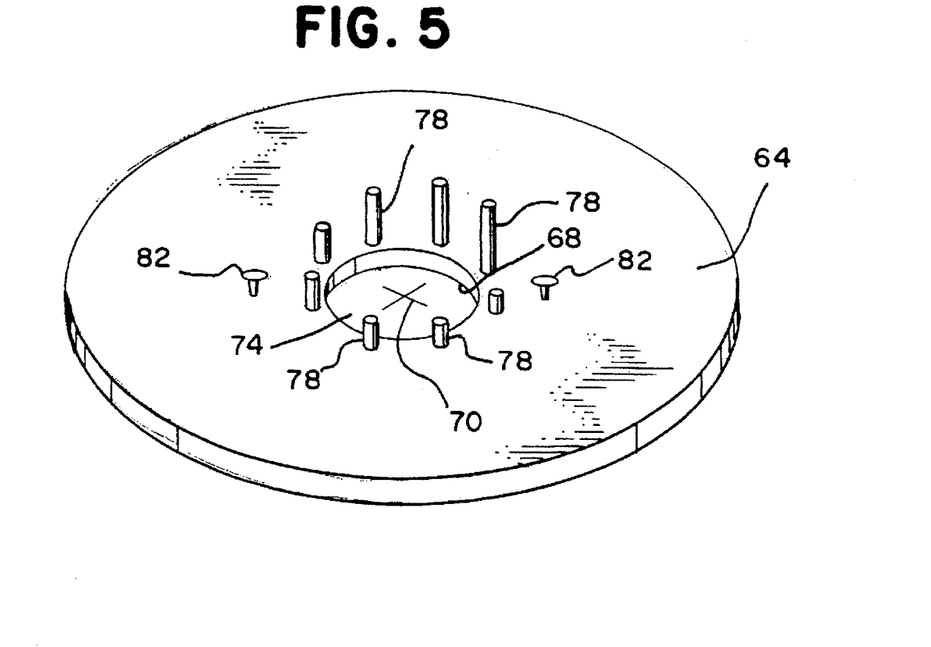
FIG. 5 is a perspective view of one of the plates comprising the invention.

In FIG. 5 another plate 64 is seen to have a shape that corresponds to the shape of the enlarged central opening 50 in plate 40. This enables plate 64 to be selectively placed in the enlarged central opening 50 of plate 40 and be supported by ledge 48.

Plate 64 includes a central opening 68 which may include cross hairs or other suitable centering means 70. The cross hairs 70 are provided so that the apparatus can be placed directly over the visual axis 24. To this extent, the cross hairs may be etched on a transparent surface 74 that is supported in central opening 68.

Surrounding the central opening are a plurality of corneal thickness sensors 78 that are arranged in a ring around the central opening 68. The diameter of the ring of sensors is somewhat larger than the optical zone 26. Preferably, the sensors 78 are pachymeters as described above.

Preferably, there are the same number of pachymeters as radial keratotomy cuts to be made so that the thickness of the cornea 14 at each cutting location will be known so that the blade of the keratotomy knife can be adjusted appropriately.

Since, a radial keratotomy procedure comprises the making of between 4 and 8 radial cuts, the plate 64 should have between 4 and 8 circumferentially spaced pachymeters, depending on the number of radial cuts that are to be made.

If desired, upwardly extending studs 82 can be provided on the plate 64 to enable it to be handled during the keratotomy procedure by simply using forceps.

Figure 6:
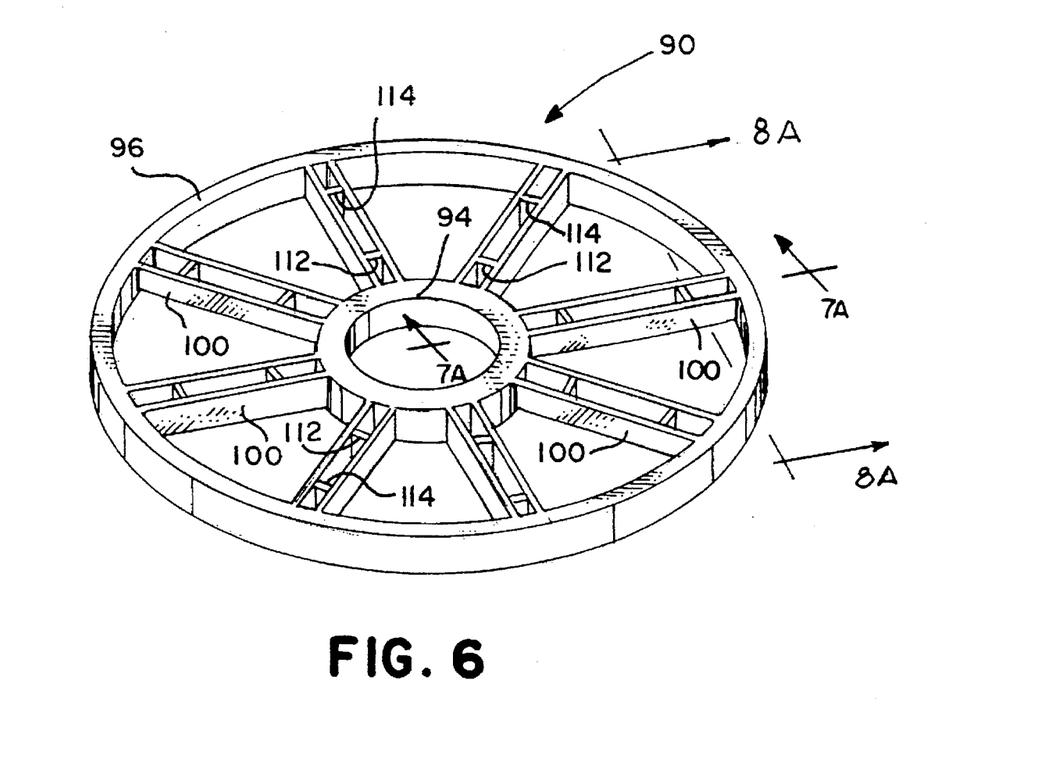
FIG. 6 is a perspective view of another plate comprising the invention.

Referring now to FIG. 6, a further plate 90 which is used for making radial keratotomy cuts in the cornea 14 is provided. The plate 90 includes inner and outer annuli 94 and 96. The outer diameter of annulus 96 is the same as that defined by the aforementioned ledge 48 in plate 40 so that plate 90 can be supported by plate 40.

A plurality of radially directed keratotomy knife guides 100 are supported between the inner and outer annuli 94 and 96. As explained earlier, between four and eight guides 100 are provided, depending on the number of radial cuts that the surgeon determines are necessary to correct the myopia.

Figure 7A:
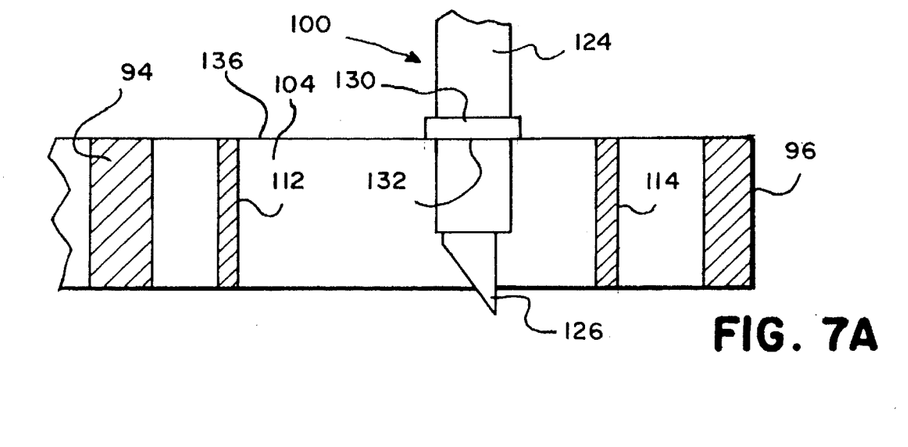
FIGS. 7A and 8A are section views taken along lines 7—7 and 8—8 of FIG. 6 that show one form of apparatus for controlling a keratotomy knife.
Figure 8A:
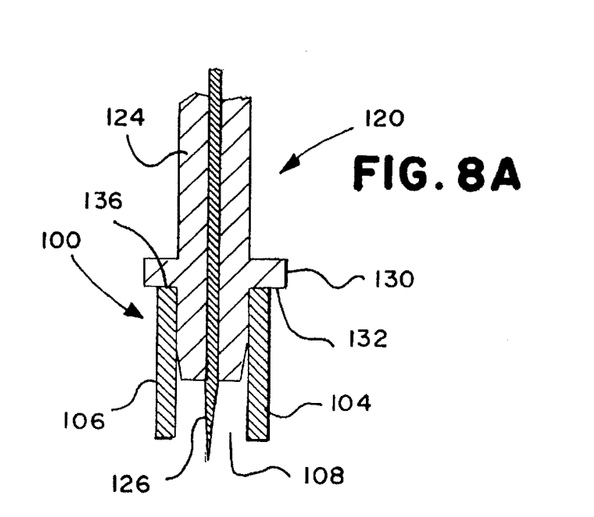

Referring to FIGS. 7A and 8A where one embodiment of keratotomy knife guides and keratotomy knife blade is shown, it is seen that each of the keratotomy knife guides 100 comprises parallel elements 104 and 106 that define a space 108 between them.

As best seen in FIG. 8A, each of the keratotomy knife guides 100 includes an inner stop 112 and a outer stop 114. The purpose of the stops is to limit the range of movement of the keratotomy knife so that neither the optical zone 26 or the sclera 16 will be inadvertently cut. However, if preferred, the separate inner and outer stops 112 and 114 could be omitted and the inner and outer annuli 94 and 96 could serve as stops. In the latter instance the third plate would have to be available with the inner annulus in different sizes to accommodate the different optical zones 26 that will be encountered in patients.

As seen in FIGS. 7A and 8A a keratotomy knife 120 may include a handle 124 and a blade 126. The extent to which the blade 126 extends from the handle 124 can be adjusted in a well known manner to limit the depth of the keratotomy cut to ninety percent of the thickness of the cornea.

The handle 124 includes cams that cooperate with camming surfaces as more fully explained below. The cams comprise laterally extending wings 130 having lower surfaces 132 that bear against camming surfaces that comprise the upper surfaces 136 of the parallel elements 104 and 106 comprising the keratotomy knife guides 100. The laterally extending wings 130 and elements 104 and 106 cooperate to control the depth to which the knife blade can penetrate after it has been adjusted.

Figure 7B:
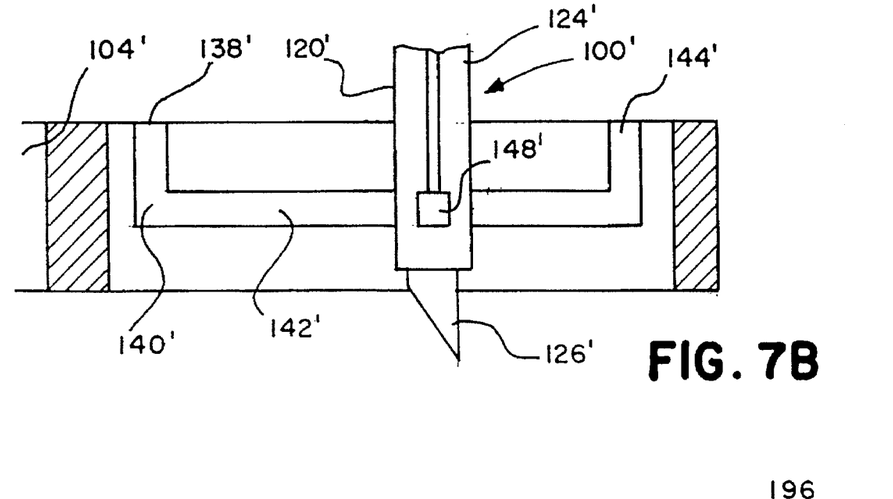
FIGS. 7B and 8B are section views taken along lines 7—7 and 8—8 of FIG. 6 that show another form of apparatus for controlling a keratotomy knife.
Figure 8B:
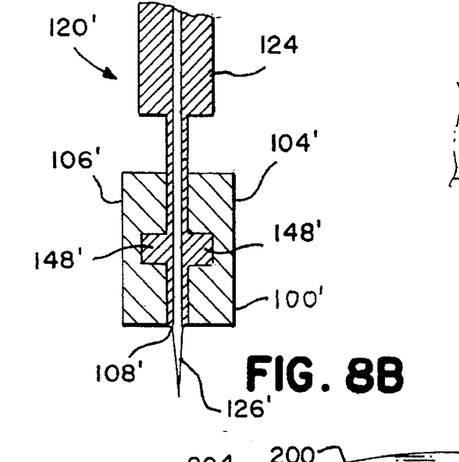

Referring to FIGS. 7B and 8B where another embodiment of the keratotomy knife guides 100 and keratotomy knife 120 is shown, it is seen that each of the keratotomy knife guides 100' comprises parallel elements 104' and 106' that define a space 108' between them.

As best seen in FIGS. 7B and 8B each of the keratotomy knife guides 100' includes camming surfaces that define a "U" shaped track 138' on the inwardly facing surfaces of the of the parallel elements 104' and 106'. Each of the "U" shaped tracks 138' includes an entry and piercing leg 140', a cutting leg 142' and a withdrawal leg 144'. The functions of the legs 140' and 144' can be interchanged since some ophthalmic surgeons make their radial keratotomy cuts toward the optical zone while others start their cuts at the optical zone and cut away from it.

The keratotomy knife 120' includes a handle 124' and a blade 126'. The extent to which the blade 126' extends from the handle 124' can be adjusted in a well known manner. The handle 124' includes cams that are received by the camming surfaces. To this extent, the cams comprise laterally extending guide blocks 148' that are received in the "U" shaped track 138'. Preferably, the legs of the "U" shaped track are all the same width and the guide blocks 148' are square in cross section and are substantially the same size as the width of the tracks so that they fit closely in the track to minimize the rocking of the keratotomy knife 120' so that it will be accurately guided as it travels through the "U" shaped tracks.

In this embodiment of the invention, legs 140' and 144' function as stops since they limit the length of the radial cut. Leg 142' functions to control the depth to which the knife blade an penetrate after it has been adjusted.

Figure 9:
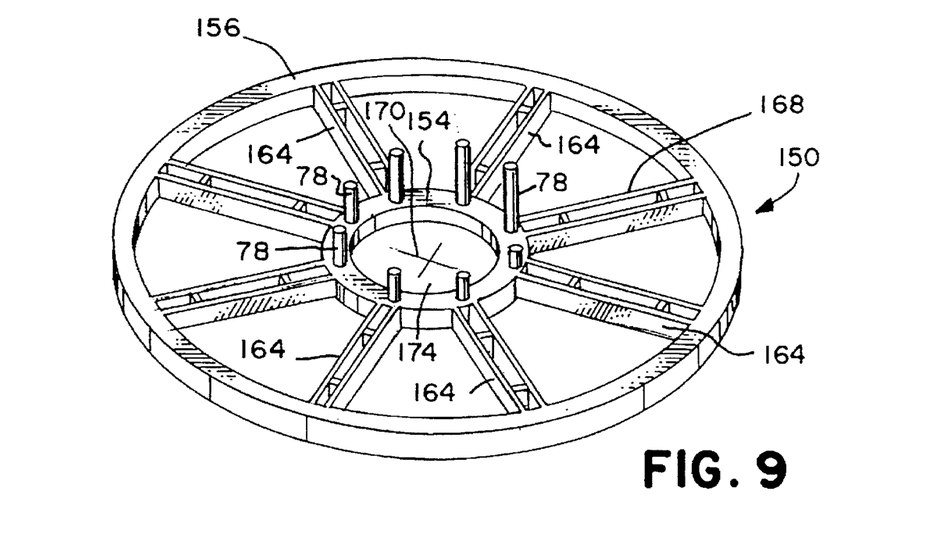
FIG. 9 is a perspective view of an alternate form of plate.

Referring now to FIG. 9, a further plate 150 is illustrated. Plate 150 combines the functions of plates 64 and 90 illustrated in FIGS. 5 and 6 respectively. Thus, plate 150 includes inner and outer annuli 154 and 156. The outside diameter of outer annulus 156 has a shape and size which is the same as that defined by the enlarged central opening 50 on plate 40 so that plate 150 can be received in the enlarged central opening 50 and be supported by ledge 48.

The inner annulus 154 is sufficiently wide to support a plurality of sensors 160 for detecting the thickness of the cornea. The diameter of the ring of sensors 78 is slightly larger than the diameter of the optical zone 26.

A plurality of keratotomy knife guides 164 of the same type as described with respect to the plate 90 in FIG. 6 are provided. There is a corneal thickness sensor 160 for each of the radial knife guides 164.

The interior of inner annulus 154 is provided with cross hairs 170 which may be supported on a transparent surface 174.

Since plate 150 in FIG. 9 combines the features of the plates 64 and 90, it can be substituted for those plates. However, in some circumstances, such a substitution may not be desirable. Thus, it is anticipated that the plate 40 will be universal in that it can support plates having different size optical zones so that it can be used for keratotomy patients of different ages and having different ophthalmic needs.

However, once the thickness of the cornea 14 and the size of the optical zone 26 are determined, a plate 64 90 having keratotomy knife guides dimensioned to meet that patient's needs must be selected and installed in plate 40.

Thus, while the ophthalmic surgeon may have available for use plates 150 of widely varying sizes it is likely that they will be relatively expensive. It is therefore desirable to minimize the cost of the apparatus by providing one plate with the corneal thickness sensors 78 and then several plates comprising radial cutting guides having different size optical zones.

Figure 10:
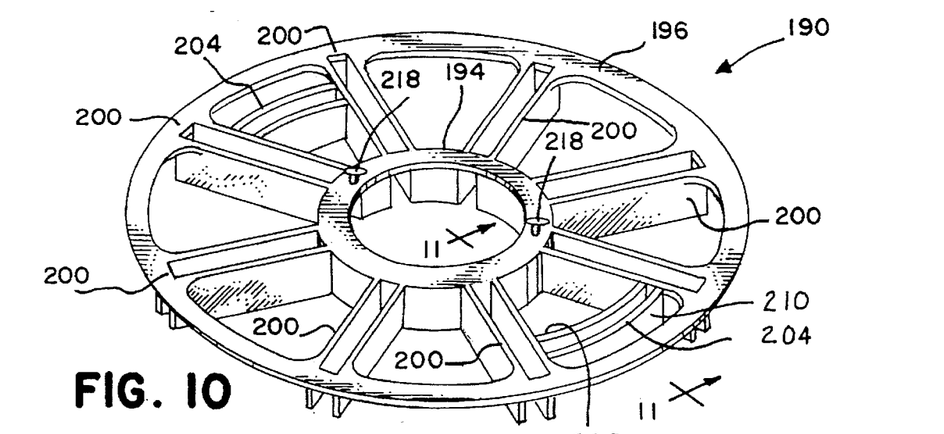
FIG. 10 is a view of another plate comprising the invention.

Referring to FIG. 10, still a further plate 190 is provided. This plate has keratotomy knife guides that are arcuately shaped so that astigmatism can be treated by making appropriate cuts in the cornea 14.

Plate 190 includes inner and outer annuli 194 and 196 that are interconnected by a plurality of radial arms 200.

Adjacent ones of the radial arms 200 that may comprise downwardly facing channels support keratotomy knife guides 204 that are arcuate. As seen in FIG. 10 the arcuate guides 204 are diametrically opposed to each other. They are spaced radially from the center of the plate 190 a distance which is sufficient to correct the astigmatism. In this regard, a plurality of plates 190 can be provided with arcuate keratotomy knife guides 204 at varying locations. Still further, the plates 190 can be provided with side-by-side arcuate keratotomy knife guides 204 so that parallel arcuate cuts can be made.

Figure 11:
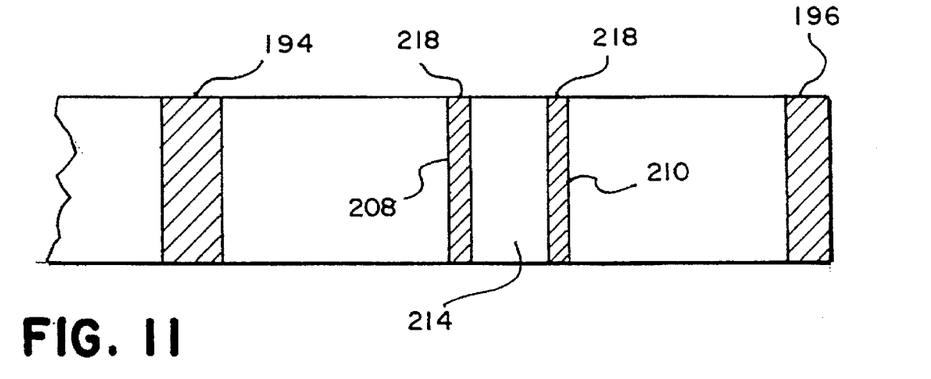
FIG. 11 is a section view taken along line 11—11 of FIG. 9.
Figure 12:
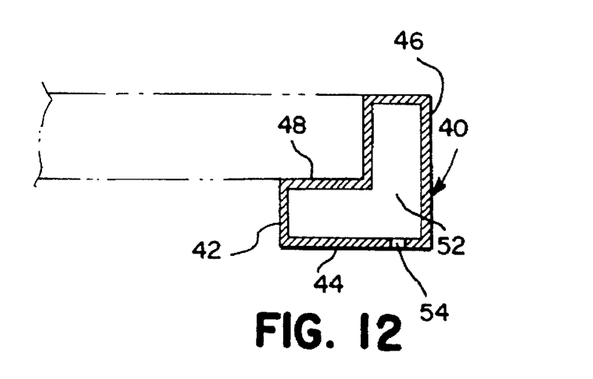
FIG. 12 is a view similar to FIG. 3 but showing the plates of the invention supported.

As seen in FIG. 11 each of the arcuate keratotomy knife guides 204 comprises an inner arcuate element 208 and an outer arcuate element 210 that define a space 214 between them.

Still further, the plates 190 can be further modified by having provisions for making four or six circumferentially spaced cuts.

In a manner similar to that described earlier, the upper surfaces 218 of the arcuate keratotomy knife guides 208 and 210 provide bearing surfaces against which the lower surfaces 132 of outwardly extending wings 130 (FIG. 7) bear to control the depth of the arcuate cuts.

If desired, the plate 190 can be provided with studs 218 similar to those described earlier.

The plate 190 can be supported on either of aforementioned plates 90 or 150. To this extent, the radial arms 200 provide guides that telescopically engage the radial keratotomy knife guides 100 and 164 on plates 190 and 150 respectively. The inner and outer annuli 194 and 196 can be relatively shallow since they merely rest on the inner and outer annuli on plates 90 and 150.

In the alternative, the inner and outer annuli 194 and 196 can be dimensioned so that the plate 190 can be received in the enlarged central opening 50 defined by ledge 48 in plate 40. However, in this form of the invention, a "key" must be provided to accurately locate the plate so that the arcuate keratotomy cuts do not intersect the radial keratotomy cuts.

It is preferred that the apparatus be supplied to the ophthalmic surgeon in kits. Thus, while only one plate 40 is needed a plurality of plates 64, 90, and 190 would be provided. This is because the size of the optical zone 26 is different in individuals, and because the radial keratotomy cuts should not enter the optical zone. In the alternative a plurality of plates 150 could be provided in lieu of plates 64 and 90. Further, the number and length of radial cuts and arcuate cuts necessary to correct myopia and/or astigmatism varies from person to person. However, for the sake of explanation, it will be assumed that these parameters have been determined and the correctly sized plates are available.

Initially, the ophthalmic surgeon first locates and marks the visual axis 24 in a well known manner.

Plate 40 is placed on the cornea 14 and plate 64 is placed on plate 40 and is supported by ledge 48.

The assembly of plates 40 and 64 is moved gently across the cornea 14 until the cross hairs 70 are directly over the visual axis 24. Air is then withdrawn from the hollow interior 52 of plate 40 to securely position the plate 40 on the cornea so that it is coaxial with the visual axis.

The sensors 78 are then energized to determine the thickness of the cornea at each of the locations where a radial cut is to be made. As explained earlier the sensors are located radially outwardly of the optical zone 26. Plate 64 is then removed from plate 40 and plate 90 is substituted for it.

Since the thickness of the cornea 14 is now known and the distance between the cornea and the upper surfaces 136 of elements 104 and 106 are known, the blade 126 can be extended from the holder 124 a distance sufficient to cut through ninety percent of the thickness of the cornea 14.

The length and location of the radial cuts are limited by the inner stop 112 and the outer stop 114. The inner stop is located radially outwardly of the optical zone 26 so that it can not be cut. Since the plate 40 remains on the cornea during the entire procedure, the plate 90 is automatically positioned so that the radial cuts are along lines that pass through the visual axis 24.

In the alternative, instead of using plates 64 and 90, the ophthalmic surgeon may elect to use a plate such as 150 which combines the functions of those two plates. In this instance, plate 150 is positioned on plate 40 with its outer annulus 156 supported by ledge 48. The corneal thickness sensors 160 are energized to determine the thickness of the cornea at each location where a radial cut is to be made. Then, the keratotomy knife is adjusted and the radial cuts are made as described earlier.

If it is necessary to correct an astigmatism, a plate 190 of suitable size is placed on plate 40 and is supported by the ledge 48. After being properly oriented so that the arcuate cuts do not intersect the radial cuts even though they are transverse to those cuts, keratotomy guides are used in a manner similar to that described.

However, there is likely to be a substantial degree of difficulty in accurately positioning plate 190 on plate 40.

Figure 13:
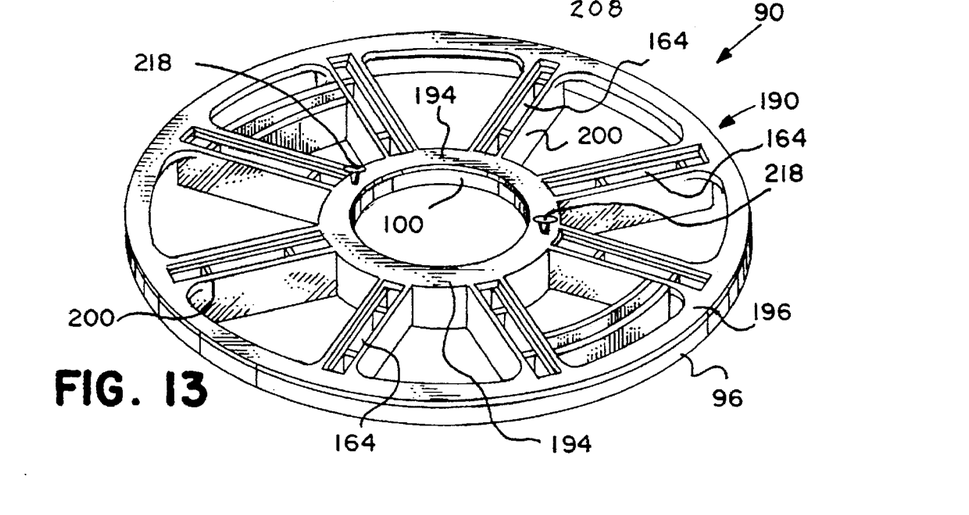
FIG. 13 is a perspective view showing two of the plates of the invention assembled.

Therefore, it is preferred that plate 190 be mounted directly on either plate 90 or plate 150 with the radial arms 200 being supported on the radial keratotomy knife guides 100 or 164 as shown in FIG. 13. To this extent, the inner annulus 194 has a diameter that is sufficiently large so that it is coextensive with or greater than the inner annuli 94 (FIG. 6) and 154 (FIG. 9). In particular, with respect to plate 150 (illustrated in FIG. 9), the inner annulus 194 on plate 190 has to be sufficiently large so that when it is placed over plate 150 it does not interfere with the corneal thickness sensors 160. One of the radial arms 200 can be higher than the others to enable it to be easily gripped by a forceps.

Further, it should be noted that the radial arms 200 on plate 190 serve two functions. One is to support the inner and outer annuli 194 and 196, and the other is to support the inner and outer arcuate guide plates 208 and 210 that comprise the arcuate keratotomy knife guides 204 so that they are between the radial keratotomy knife guides 100 and 164.

After the procedure is complete, the ophthalmic surgeon then terminates the vacuum and then quickly and easily removes the plate 40 and whichever of the other plates are on it from the cornea 14.

Figure 14:
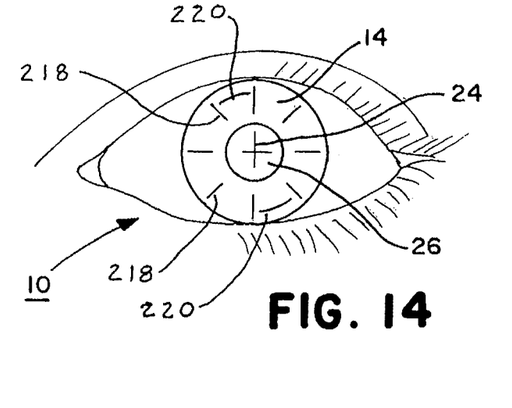
FIG. 14 is a plan view of an eye showing the keratotomy cuts.

The treated eye 10 is shown in FIG. 14 where it can be seen that eight radially directed cuts 218 and two diametrically opposed arcuate cuts 220 have been made in the cornea 14.

Thus, what has been described is an apparatus and a method that permits an ophthalmic surgeon to quickly and easily perform both radial and astigmatic keratotomies with a minimum likelihood of error and/or accident.

The apparatus can be supplied in kits where the plates that comprise the keratotomy knife guides having optical zones 26 of different sizes to accommodate the needs of patients.

While the invention has been described with respect to certain forms, it is apparent that other forms will be obvious to those skilled in the art in view of the description. Thus, the scope of the invention should not be limited by the description, but, only by the appended claims.

What is claimed is:

1. An apparatus for performing a keratotomy on an eye, said eye having a cornea, an optical zone and a visual axis, said apparatus comprising a first plate, said first plate including means for positioning said first plate over the visual axis and means for retaining said first plate over the visual axis;

a second plate, said second plate including means for measuring the thickness of the cornea;

a third plate, said third plate having a first plurality of keratotomy knife guides; and said first plate includes means for selectively carrying said second and third plates so that said second plate can be replaced by said third plate on said first plate after the thickness of the cornea is measured to enable said keratotomy knife guides to be aligned on the visual axis.

2. An apparatus as defined in claim 1 including a fourth plate, said fourth plate having a second plurality of keratotomy knife guides, said second plurality of keratotomy knife guides extending in a direction that is transverse to the direction of said first plurality of keratotomy knife guides.

3. An apparatus as defined in claim 2 wherein said third and fourth plates include mutually engaging means that cooperate to enable one of said third and fourth plates to be supported on the other of said third and fourth plates so that after keratotomy cuts in the cornea are made in one of said directions keratotomy cuts in the cornea can be made in the other of said directions.

4. An apparatus as defined in claim 3 wherein said third plate includes a plurality of radially extending keratotomy knife guides;

said fourth plate includes a plurality of radially directed guides;

an arcuate keratotomy knife guide disposed between adjacent ones of said radially directed guides; and said radially extended keratotomy knife guides are receivable in said radially directed guides so that said fourth plate can be supported by said third plate.

5. An apparatus as defined in claim 2 including a keratotomy knife, and means on said keratotomy knife for engaging said keratotomy knife guides.

6. An apparatus as defined in claim 5 wherein said keratotomy knife guides comprise spaced parallel elements, and the distance between said elements corresponds to the thickness of the blade of said keratotomy knife.

7. An apparatus as defined in claim 6 wherein said keratotomy knife includes a holder and a blade, said blade being supported by said holder;

said keratotomy knife guides including means for limiting the depth to which said blade can cut into the cornea; and complementary means on said keratotomy knife for engaging said means for limiting the depth to which said blade can cut into the cornea.

8. An apparatus as defined in claim 7 wherein said means for limiting the depth to which said blade can cut into the cornea comprises the distal edges of said complementary means on said keratotomy knife.

9. An apparatus as defined in claim 7 wherein said complementary engaging means is on said holder.

10. An apparatus as defined in claim 7 wherein said means for limiting the depth to which said blade can cut into the cornea comprises opposed recesses on the inwardly facing surfaces of said keratotomy knife guides; and complementary engaging means on said keratotomy knife.

11. An apparatus as defined in claim 10 wherein said complementary engaging means is on said holder.

12. An apparatus as defined in claim 1 wherein said first plate comprises an annulus and said means for retaining said first plate in position comprises a plurality of openings circumferentially disposed around said annulus and means for drawing a vacuum through said openings.

13. An apparatus as defined in claim 1 wherein said means for measuring the thickness of the cornea comprises a plurality of sensors that are disposed in a ring, said ring having a diameter that corresponds to the diameter of the optical zone; and said first and second plates have mutually engagable means that cooperate to locate said ring of sensors radially outwardly of said optical zone, and with its center on the visual axis.

14. An apparatus as defined in claim 13 wherein said means for measuring the thickness of the cornea comprises a plurality of sensors that are disposed in a ring, said ring having a diameter that corresponds to the diameter of the optical zone;

said first and second plates have mutually engagable means that cooperate to locate said ring of sensors radially outwardly of said optical zone, and with its center on the visual axis; and each of said sensors lies along one of said lines that pass through the visual axis.

15. An apparatus as defined in claim 1 wherein said first plurality of keratotomy knife guides extends radially outwardly along lines that passes through the visual axis.

16. An apparatus as defined in claim 15 wherein said second plurality of keratotomy knife guides comprise arcs that extend along the circumference of a circle whose center is at the visual axis.

17. An apparatus as defined in claim 16 wherein said circle lies outside of the optical zone.

18. An apparatus as defined in claim 16 wherein said second plurality of keratotomy knife guides are disposed between adjacent ones of said radial keratotomy knife guides.

19. An apparatus as defined in claim 1 wherein said keratotomy knife guides comprise spaced parallel elements, and the distance between said elements corresponds to the thickness of the blade of a keratotomy knife.

20. An apparatus as defined in claim 19 wherein said keratotomy knife guides extend radially along lines that pass through the visual axis; and each of said keratotomy knife guides includes an inner stop near the optical zone for preventing a knife from cutting the optical zone.

21. An apparatus as defined in claim 20 wherein each of said keratotomy knife guides includes an outer stop that is spaced from said inner stop;

said outer stop and said inner stop being operative to define the length of the cut made by the keratotomy knife.

22. A method of performing keratotomy on the eye comprising the steps of locating the optical axis of the eye;

providing a plurality of keratotomy knife guides;

spacing said keratotomy knife guides from the optic zone of the eye; and making arcuate and radial keratotomy cuts in the cornea at the locations defined by said keratotomy knife guides, and disposing said arcuate keratotomy cuts between said radial keratotomy cuts.

23. A method as defined in claim 22 including the step of making said arcuate keratotomy cuts after said radial keratotomy cuts are made.

24. An apparatus for performing a keratotomy on an eye, said eye having a cornea, an optical zone and a visual axis, said apparatus comprising a first plate, said first plate including means for supporting a second plate;

means for positioning said first plate over the visual axis;

said first plate including means for being retained over the visual axis;

a second plate, said second plate having a first plurality of keratotomy knife guides;

said second plate being receivable on said first plate after said first plate is retained over the visual axis;

a third plate, said third plate having a second plurality of keratotomy knife guides, said second plurality of keratotomy knife guides extending in a direction that is transverse to the direction of said first plurality of keratotomy knife guides; and said first plate includes means for selectively carrying said second and third plates so that said second plate can be replaced by said third plate to enable said second plurality of keratotomy knife guides to be positioned over the cornea.

25. An apparatus for performing a keratotomy on an eye, said eye having a cornea, an optical zone and a visual axis, said apparatus comprising a first plate, said first plate including means for supporting a second plate;

means for positioning said first plate over the visual axis;

said first plate including means for being retained over the visual axis;

a second plate, said second plate having a first plurality of keratotomy knife guides;

said second plate being receivable on said first plate after said first plate is retained over the visual axis;

a fourth plate, said fourth plate including means for measuring the thickness of the cornea; and said fourth plate is receivable on said first plate after said first plate is retained over the visual axis.

26. An apparatus for performing a keratotomy on an eye, said eye having a cornea, an optical zone and a visual axis, said apparatus comprising a first plate, said first plate including means for supporting a second plate;

means for positioning said first plate over the visual axis;

said first plate including means for being retained over the visual axis;

a second plate, said second plate having a first plurality of keratotomy knife guides;

said second plate is receivable on said first plate after said first plate is retained over the visual axis;

a third plate, said third plate having a second plurality of keratotomy knife guides, said second plurality of keratotomy knife guides extending in a direction that is transverse to the direction of said first plurality of keratotomy knife guides; and said third plate includes means for engaging said second plate so that said third plate can be supported on said second plate.

27. An apparatus for performing a keratotomy on an eye, said eye having a cornea, an optical zone and a visual axis, said apparatus comprising a keratotomy knife, and said keratotomy knife including cams;

a first plate, said first plate including means for supporting a second plate;

means for positioning said first plate over the visual axis;

said first plate including means for being retained over the visual axis;

a second plate, said second plate being receivable on said first plate after said first plate is retained over the visual axis, said second plate having a first plurality of keratotomy knife guides, said keratotomy knife guides comprising spaced parallel elements having facing camming surfaces; and said cams on said keratotomy knife cooperate with said camming surfaces to control the depth of the keratotomy cuts.

28. An apparatus for performing a keratotomy on an eye, said eye having a cornea, an optical zone and a visual axis, said apparatus comprising a keratotomy knife, and said keratotomy knife includes laterally extending cams, a first plate, said first plate including means for supporting a second plate;

means for positioning said first plate over the visual axis;

said first plate including means for being retained over the visual axis;

a second plate, said second plate being receivable on said first plate after said first plate is retained over the visual axis;

said second plate having a first plurality of keratotomy knife guides comprising opposed "U" shaped tracks;

one of the legs of said "U" shaped track defining and inner stop, another leg of said "U" shaped track defining an outer stop, and said third leg controlling the depth of the keratotomy cut; and said laterally extending cams on said keratotomy knife cooperate with said "U" shaped tracks to control the depth of the keratotomy cuts.

29. An apparatus as defined in claim 28 wherein the legs of said "U" shaped tracks are all the same width, and said cams are square in cross section and are substantially the same size as said width of said tracks so that said cams closely fit in said tracks to minimize the rocking of said keratotomy knife.

30. A first plate for use in a keratotomy apparatus comprising inner and outer annular members, said members being generally concentric;

a plurality of keratotomy knife guides, said keratotomy knife guides being radially directed and extending between said inner and outer annular members, and means supported on said first plate for measuring the thickness of the cornea, said last named means lying radially outward of the optical zone.

31. A method of performing keratotomy on the eye comprising the steps of locating the optical axis of the eye;

providing a plurality of arcuate keratotomy knife guides;

spacing said arcuate keratotomy knife guides from the optic zone of the eye; and making arcuate keratotomy cuts in the cornea at the locations defined by said arcuate keratotomy knife guides.

32. A method as defined in claim 31 including providing a plurality of radial keratotomy knife guides, making radial keratotomy cuts in the cornea at the locations defined by said radial keratotomy knife guides, and said arcuate keratotomy cuts are disposed between said radial keratotomy cuts.

33. A method as defined in claim 32 wherein said arcuate keratotomy cuts are made after said radial keratotomy cuts are made.

34. A method of performing keratotomy on the eye comprising the steps of locating the optical axis of the eye;

providing a plurality of keratotomy knife guides;

spacing said keratotomy knife guides from the optic zone of the eye;

measuring the thickness of the cornea before making said keratotomy cuts, and making keratotomy cuts in the cornea at the locations defined by said keratotomy knife guides.

35. A method as defined in claim 34 wherein a plurality of radial keratotomy cuts are made; and the thickness of the cornea is measured at the location of each of said radial cuts.

* * * * *